(12) United States Patent
Richter

(10) Patent No.: US 7,785,319 B2
(45) Date of Patent: *Aug. 31, 2010

(54) METHOD AND APPARATUS FOR TREATING BODILY TISSUES WITH MEDICINAL SUBSTANCE

(75) Inventor: Jacob Richter, Ramat Hasharon (IL)

(73) Assignee: Microtech Medical Technologies Ltd., Tel Aviv (IL)

( * ) Notice: Subject to any disclaimer, the term of this patent is extended or adjusted under 35 U.S.C. 154(b) by 630 days.

This patent is subject to a terminal disclaimer.

(21) Appl. No.: 11/142,161

(22) Filed: May 31, 2005

(65) Prior Publication Data

US 2005/0222627 A1    Oct. 6, 2005

Related U.S. Application Data

(63) Continuation of application No. 10/348,100, filed on Jan. 21, 2003, now Pat. No. 6,969,382, which is a continuation-in-part of application No. 09/964,836, filed on Sep. 26, 2001, now abandoned, which is a continuation of application No. 09/360,893, filed on Jul. 26, 1999, now Pat. No. 6,334,859.

(51) Int. Cl.
    *A61K 9/22* (2006.01)
(52) U.S. Cl. .................................... 604/890.1
(58) Field of Classification Search ............ 604/19, 604/20, 21, 890.1, 891.1, 501, 502, 503, 604/93.01; 606/32; 607/62, 115, 116
    See application file for complete search history.

(56) References Cited

U.S. PATENT DOCUMENTS

| | | | |
|---|---|---|---|
| 4,041,954 A | 8/1977 | Ohara | |
| 4,351,337 A * | 9/1982 | Sidman | 424/425 |
| 4,585,652 A | 4/1986 | Miller et al. | |
| 4,611,596 A | 9/1986 | Wasserman | |
| 4,651,740 A | 3/1987 | Schroeppel | |
| 4,657,543 A | 4/1987 | Langer et al. | |
| 4,944,659 A | 7/1990 | Labbe et al. | |
| 5,041,107 A * | 8/1991 | Heil, Jr. | 604/891.1 |
| 5,298,017 A | 3/1994 | Theeuwes et al. | |
| 5,304,206 A | 4/1994 | Baker et al. | |
| 5,366,454 A | 11/1994 | Currie et al. | |
| 5,411,535 A | 5/1995 | Fujii et al. | |
| 5,421,816 A | 6/1995 | Lipkovker | |
| 5,431,694 A | 7/1995 | Snaper et al. | |
| 5,551,953 A * | 9/1996 | Lattin et al. | 604/20 |
| 5,647,844 A * | 7/1997 | Haak et al. | 604/20 |
| 5,656,016 A * | 8/1997 | Ogden | 601/2 |
| 5,741,317 A | 4/1998 | Ostrow | |
| 5,749,909 A * | 5/1998 | Schroeppel et al. | 607/33 |
| 5,797,898 A | 8/1998 | Santini, Jr. | |
| 5,807,306 A | 9/1998 | Shapland et al. | |
| 5,893,840 A | 4/1999 | Hull et al. | |
| 6,529,777 B1 | 3/2003 | Holmstrom et al. | |
| 6,768,919 B2 | 7/2004 | Starobin et al. | |
| 6,969,382 B2 * | 11/2005 | Richter | 604/890.1 |

FOREIGN PATENT DOCUMENTS

| | | |
|---|---|---|
| EP | 0 061 783 | 10/1982 |
| EP | 0 495 531 | 7/1992 |
| EP | 1 072 283 | 1/2001 |
| JP | 61-196967 | 9/1986 |
| JP | 02-058426 | 8/1988 |
| JP | 02-19147 | 1/1990 |
| JP | 2-144077 | 6/1990 |
| JP | 2-152468 | 6/1990 |
| JP | 2-152469 | 6/1990 |
| JP | 5-220222 | 8/1993 |
| JP | 5-245215 | 9/1993 |
| JP | 5-329482 | 12/1993 |
| JP | 10-503960 | 4/1998 |
| RU | 94/027257 | 5/1996 |
| RU | 2082467 | 6/1997 |
| WO | WO 88/05314 | 7/1988 |
| WO | WO 93/09841 | 5/1993 |
| WO | WO 94/21314 | 9/1994 |
| WO | 96/13302 | 5/1996 |
| WO | WO 96/13302 A | 9/1996 |
| WO | WO 99/39768 | 8/1999 |
| WO | WO 00/12062 | 3/2000 |
| WO | 01/07110 | 2/2001 |
| WO | WO 01/07110 A2 | 2/2001 |
| WO | 2004/065541 | 8/2004 |

OTHER PUBLICATIONS

EP Supplemental Search Report.
Partial European Search Report dated Apr. 21, 2009, 9-pages, from co-pending application No. EP 08008616.8, published as EP 2 027 887.

* cited by examiner

*Primary Examiner*—Nicholas D Lucchesi
*Assistant Examiner*—Christopher D Koharski
(74) *Attorney, Agent, or Firm*—Cadwalader Wickersham & Taft LLP

(57) ABSTRACT

A therapeutic device and therapeutic method for delivering electrical energy to a polymer containing a medicament that allows release of the medicament to a body tissue or organ. The device and method utilizes ultrasonic vibrations to cause the device, implanted in the body tissue or organ to be treated, to discharge an electrical current to the polymer containing the medicament. The medicament is controllably released to the target area by changing the charge of the polymer with the electrical current.

17 Claims, 7 Drawing Sheets

METHOD AND APPARATUS FOR TREATING BODILY TISSUES WITH MEDICINAL SUBSTANCE

CROSS REFERENCE TO RELATED APPLICATIONS

This is continuation of application Ser. No. 10/348,100, filed Jan. 21, 2003 now U.S. Pat. No. 6,969,382 which is a CIP of Ser. No. 09/964,836 filed Sep. 26, 2001 now abandoned which is a continuation of Ser. No. 09/360,893 filed Jul. 26 1999, now issued as U.S. Pat. No. 6,334,859.

FIELD OF INVENTION

The method and apparatus generally relates to implanted devices which are placed within the body of a living animal or human to impart a therapeutic benefit to a target tissue or organ, and more particularly to a device and method for selectively delivering a medicament to a target tissue or organ by applying an electrical current to a polymer to cause release of the medicament from the polymer.

BACKGROUND

Many disorders, e.g., brain disorders and certain types of paralysis, as well as reduction of restenosis during angioplasty procedures, are treated by an electrical stimulus or local drug delivered to specific sites in the brain or other parts of the body. One shortcoming of conventional treatment devices and procedures is that conventional treatment devices are large and their placement may cause damage to the patient or that the release of drug at a desired pace is impossible or difficult. Another shortcoming of conventional treatment devices and procedures is that the devices are often implanted and must remain connected to the outside world for their control signal or energy supply. In addition, in conventional devices and procedures, drug delivery to the target tissue may cause trauma to the patient and may not be precisely delivered to the target tissue, and, where there is a physical connection to the outside world, the repeated trauma to the patient required by repeated invasion and introduction of foreign objects into the tissue increases the likelihood of infection. Yet another shortcoming of conventional devices and procedures is that they do not provide precise timing of the delivery of the electrical stimulus or drug in response to phenomena happening in, and to stimuli generated by, the tissue or the organ being treated indicating the need for the delivery of such an electrical stimulus or drug.

In recent years, controlled drug delivery systems utilize an implant made of a polymer, either natural or synthetic, that is combined with a drug or other active agent in such a way that the active agent is released in a pre-determined manner. For example, the release of the active agent may be constant over a long period, or it may be cyclic over a sustained period of time. It may be triggered by the environment or other external stimulus. In any case, the purpose behind controlling the drug delivery is to achieve more effective therapies while eliminating the potential for under-dosing or over-dosing.

There are three primary mechanisms by which active agents can be released from such a delivery system: diffusion, degradation, and swelling followed by diffusion. Each of these mechanisms, however, has disadvantages when employed as a delivery mechanism. In the case of diffusion, the disadvantage is that as the release progresses, the release rate will decrease, because the active agent concentration in the polymer decreases, and the agent has a progressively longer distance to travel, thus, the diffusion time to relevant tissue will increase. In the case of degradation, the process generates degradation by-products that may not be tolerated within the biological environment causing inflammatory reactions that may lead to adverse effects. Finally, for the swelling/degradation approach, drug release will be accomplished only when the polymer swells. The drug may prematurely be released upon contact of bodily fluid outside the target area. In addition, the drug may not be released at all if the target area does not contain a suitable environment to facilitate drug release, e.g., will not cause sufficient swelling. All adverse effect risks of the degrading polymer exist here also.

While advantages of these current drug delivery systems can be significant, their potential disadvantages or limitations cannot be ignored: the decreased rate of drug release over time, the possible toxicity or non-bio-compatibility of the materials used, undesirable by-products of degradation, and the potential for both under-dosing and overdosing. Thus, there remains a need for an improved drug delivery system that is inert, biocompatible, safe from accidental release, and capable of providing a consistent rate of drug release.

SUMMARY OF THE INVENTION

It is an object of this invention to provide an apparatus and method for selectively delivering a medicament over a period of time to a target tissue or organ of the body, e.g., the brain or treated arteries, without creating a large lesion in the target area and without requiring a connection to the outside world, for example outside the patient's body.

It is yet another object of this invention to release a medication from a polymer at a desired rate by applying current or charge to the polymer containing the medication.

It is yet another object of this invention to provide a method of treating body tissue, comprising the steps of preparing a device capable of generating electrical current at a therapeutic voltage and amperage in response to ultrasonic vibrations; disposing the device in the vicinity of the tissue to be treated; and subjecting the device to ultrasonic vibrations in an amount and for a period of time sufficient for the device to generate electrical currents at a therapeutic voltage and amperage.

It is a further object of this invention to provide a device for treating body tissue, comprising a housing provided with a medicament storage compartment. An oscillating member is attached to the housing and communicates with the medicament storage compartment and is adapted to oscillate in response to ultrasonic stimulation. A medicament port is disposed on the housing and is in fluid communication with the medicament storage compartment and is adapted to permit a medicament to be introduced into and contained in the compartment. The medicament port is further adapted to selectively release the medicament from the medicament storage compartment in response to the oscillations of the oscillating member which produce a "pumping" action to pump the medicament out of the compartment in response to external high frequency stimulation.

It is still a further object of this invention to provide a method of treating body tissue, comprising the steps of preparing a device comprising a housing provided with a medicament storage compartment. An oscillating member is attached to the housing and is in fluid communication with the medicament storage compartment and is adapted to oscillate in response to ultrasonic stimulation. A medicament port is disposed on the housing and communicates with the medicament storage compartment and is adapted to permit a medicament to be introduced into and contained in the compartment. The medicament port is further adapted to selectively release the medicament from the medicament storage compartment in response to oscillations of the oscillating member. In operation, a medicament is introduced through the medicament port and into the medicament storage compartment. The device is disposed in the vicinity of the tissue to be treated and is subjected to ultrasonic vibrations in an amount and for a period of time sufficient for the oscillating member to oscillate in an amount and for a period of time to cause the desired quantity medicament to be discharged from the medicament storage compartment through the medicament port to the tissue to be treated.

It is yet another object of this invention to provide a sensor or an array of sensors communicating with a tissue or organ being treated, e.g., the brain, or other excitable tissues in the body. The sensors communicate with one or more actuators adapted to selectively deliver a predetermined amount of an electrical impulse or a medicament to the tissue or organ being treated in response to the sensed stimulus generated by the tissue or organ being treated indicating the need for the delivery of such an electrical impulse or medicament. In an especially preferred embodiment, the stimulation is sensed in one tissue, e.g., the brain or a nerve and the stimulation occurs in a different tissue, e.g., a paralyzed leg muscle.

It is yet another object of this invention to provide a method of treating body tissue or organ, comprising the steps of preparing a device capable of generating electrical current at a specific voltage and amperage in response to ultrasonic vibrations; disposing the device in the vicinity of the tissue to be treated; and subjecting the device to ultrasonic vibrations in an amount and for a period of time sufficient for the device to generate electrical currents at a specific voltage and amperage towards a polymer containing a medicament for causing controlled release of the drug from the polymer.

DETAILED DESCRIPTION OF THE INVENTION

Miniature Oscillating Ceramic Motors (OCM) are well known in the art and are disclosed in U.S. Pat. No. 5,453,653 to Zumeris the specification of which is incorporated herein by reference. These motors can be made very small and in any shape and they operate by contacting a surface in an amount sufficient to generate sufficient friction to permit the motor to "crawl" along the contacted surface and change its position relative to the contacted surface when the motor is energized. These motors can be adequately insulated to act in aqueous environments. Their small size and low energy level requirements make them especially suitable for use inside living organisms.

Figure 1:
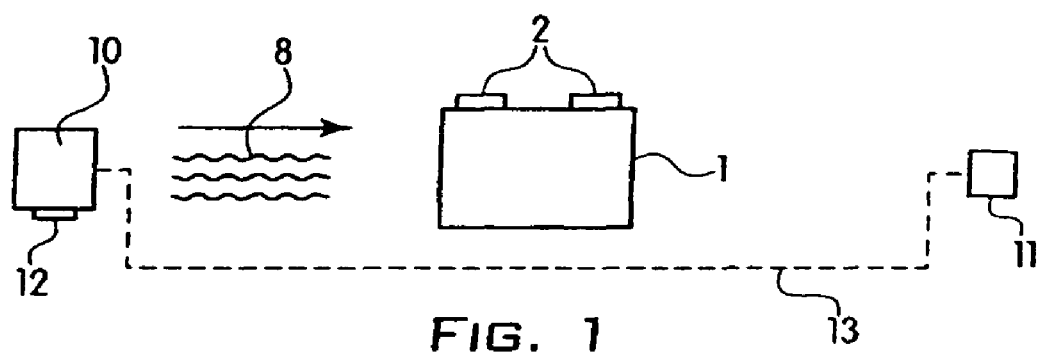
FIG. 1 shows a device constructed in accordance with the invention for applying electrical stimulation to a target tissue.

FIG. 1 shows one embodiment of a ceramic motor used in accordance with the invention to provide electrical stimulation to a target tissue. The electrical stimulation device 1 is provided with electrodes 2. In normal use, electricity is applied to the electrodes 2, which causes the electrical stimulation device 1 to generate oscillations in the ultrasonic range. It is well known that if a conventional electric motor is turned it will produce electricity. Similarly, if the ceramic motor is ultrasonically vibrated an electrical current will be generated and discharged from the electrodes 2. The ceramic motor works according to the second piezo-electric effect, and the reverse, generation of current by vibrating the ceramic is equivalent to the first piezo-electric effect. The frequencies utilized in the various embodiments of this invention may be varied as specific applications dictate. A wide range of frequencies, e.g., radio frequency (rf) or ultrasound (us), may be utilized depending upon the type and the location of the tissue being treated and the type and amount of tissue through which the high frequency vibrations must pass.

The stimulation of nerve cells in the brain system and elsewhere in the body is desirable for the treatment of different disorders, e.g., the activation of muscles whose biological activation is impaired. In application, the device will be delivered to the target area to be treated, e.g., the brain, using conventional procedures such as catheter delivery or surgical implant. Because the electrical stimulation device 1 is small there is minimal trauma to the patient. In addition, because the electrical stimulation device 1 is left in place there is a reduced likelihood of complications or tissue damage that might result from repeated invasion, e.g., by needles or electrodes repeatedly introduced and removed from the target area. Furthermore, because there is no need for the electrical stimulation device 1 to remain connected to the outside world after it has been implanted, there is a reduced likelihood of complications, e.g., infection, that may result from the connection to the outside world.

Once the electrical stimulation device 1 is in place it is subjected to ultrasonic energy 8 from a means 10 for selectively generating ultrasonic vibrations 8 which causes the electrical stimulation device 1 to vibrate and generate electricity from the electrodes 2. The electrodes 2 may be sized and disposed on the device as specific applications dictate to maximize the effectiveness of the treatment. The electrical stimulation device 1 and the treatment time may be modified to generate electricity at a desired voltage and amperage and for a desired period of time as specific applications dictate.

Figure 2:
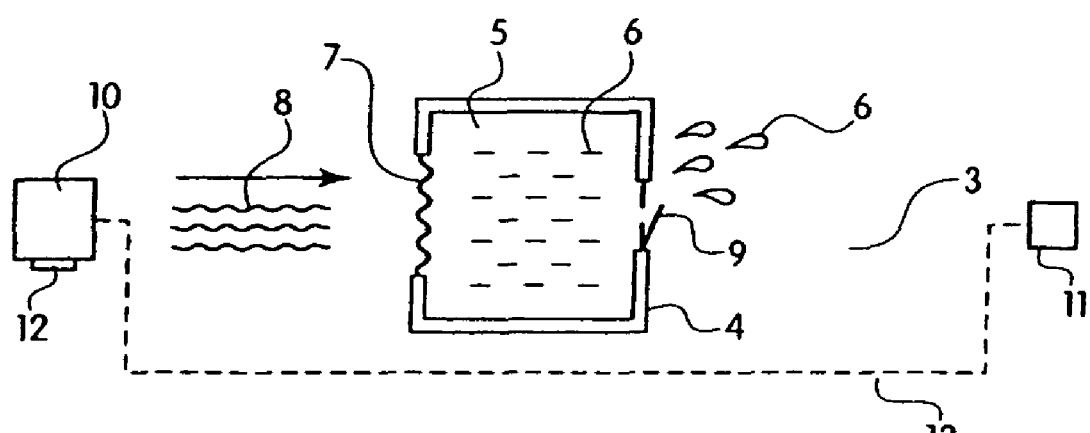
FIG. 2 shows a device constructed in accordance with the invention for delivering a medicament to a target tissue.
Figure 3:
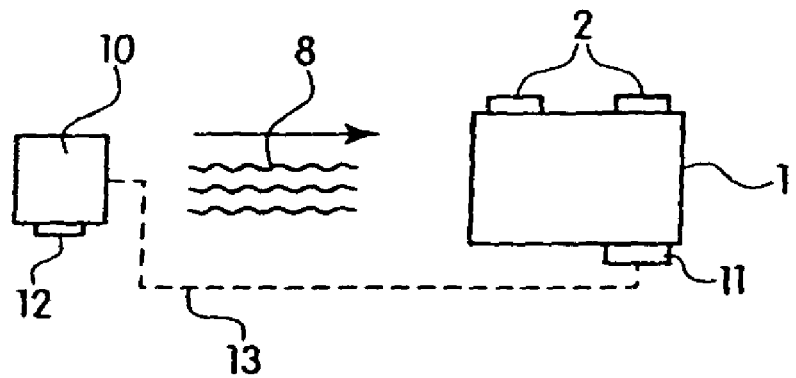
FIG. 3 shows an alternative embodiment of the device shown in FIG. 1.
Figure 4:
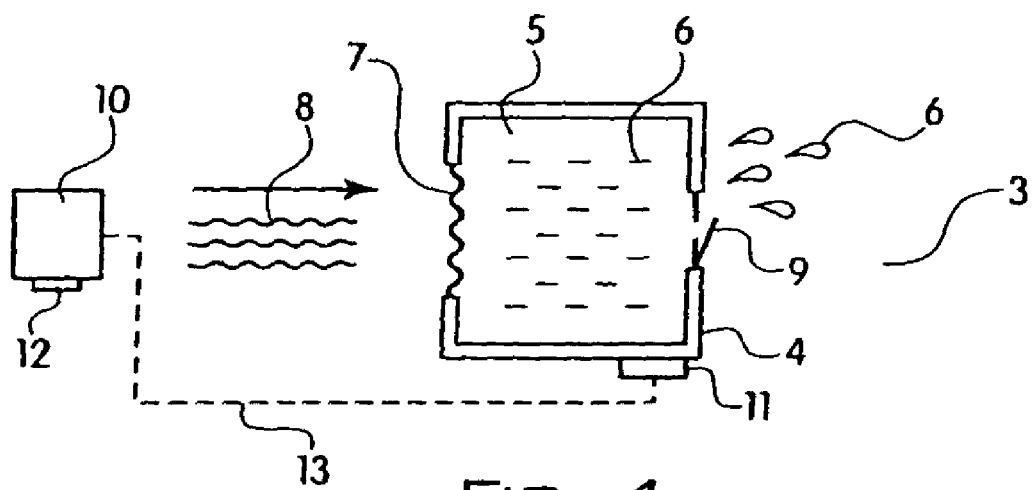
FIG. 4 shows an alternative embodiment of the device shown in FIG. 2.

FIG. 2 shows a medicament delivery device 3 constructed in accordance with the invention. FIG. 2 shows that medicament delivery device 3 is provided with housing 4 provided with a medicament storage compartment 5 for storing a medicament 6. The housing 4 is also provided with an oscillating member 7 constructed of a material that is adapted to oscillate in response to ultrasonic stimulation 8. The oscillating member 7 communicates with the medicament storage compartment 5 so that the oscillating member 7 will contact a medicament 6 stored in the medicament storage compartment 5. The housing 4 is also provided with a medicament port 9 in fluid communication with the medicament storage compartment 5. The medicament port 9 is adapted to permit a medicament 6 to be introduced into the medicament storage compartment 5 and is further adapted to permit the medicament 6 to be discharged from the medicament storage compartment 5 when the oscillating member 7 oscillates. A wide variety of ports or valves well known to those skilled in the art as suitable for this purpose may be utilized; however, in a preferred embodiment an elastic flap valve shown at 9 in FIG. 2 is utilized.

In operation, the physician will introduce the medicament 6 into the medicament storage compartment 5 through the medicament port 9. The medicament delivery device 3 is then introduced into the target area using conventional procedures as previously discussed. As shown in FIG. 2, the physician may subject the medicament delivery device 3 to ultrasonic energy 8 generated by a source 10 for selectively generating and transmitting ultrasonic vibrations 8 to the oscillating member 7. The ultrasonic energy 8 impinging upon the oscillating member 7 causes the oscillating member 7 to oscillate as shown in FIG. 2. This causes the desired amount of medicament 6 to be discharged from the medicament storage compartment 5 through the medicament port 9 to the target area. The amount of time that the device 3 is exposed to the ultrasonic vibration 8 can be varied as specific applications dictate and will depend upon factors such as the target area to be treated, the quantity of medicament 6 to be delivered, and the composition, e.g., solid or liquid and/or the viscosity of the medicament 6.

In utilizing both the electrical stimulation device 1 and the medicament delivery device 3, the source for generating the ultrasonic vibrations 10 may be manually operated; it may be programmed to generate ultrasonic vibrations for a predetermined fixed period of time, e.g., 10 seconds, at predetermined fixed intervals, e.g., every hour; or it may be automatically energized in response to signals received from a sensor 11.

In a particularly advantageous embodiment, one or more sensors 11 may be utilized in conjunction with the devices 1 and 3 as shown in FIGS. 1 to 6 to monitor the tissue being treated for a variety of preselected physiological activities and parameters which indicate the need for treatment and the amount of treatment required. These physiological activities and parameters include, e.g., but are not limited to, changes in neurological activity, temperature, pressure, fluid discharge from the target area, chemical composition of the discharge, and chemical changes in the tissue being treated.

The sensor or sensors 11 may be implanted at several points on or in the tissue or organ being treated as specific applications dictate. Alternatively, the sensor 11 may be disposed on the actual devices 1 and 3 (as shown in FIGS. 3-6). The sensor 11 is adapted to communicate with the source 10 for selectively generating and transmitting ultrasonic vibrations 8 as previously discussed. The communication link 13 between the sensor 11 and the source 10 may be a direct one, e.g., an electrical lead, or, it may occur via radio transmission. Radio communication between the sensor 11 and the source 10 may be preferable because it reduces discomfort to the patient and also reduces the likelihood of infection otherwise caused by a wire connection.

Figure 5:
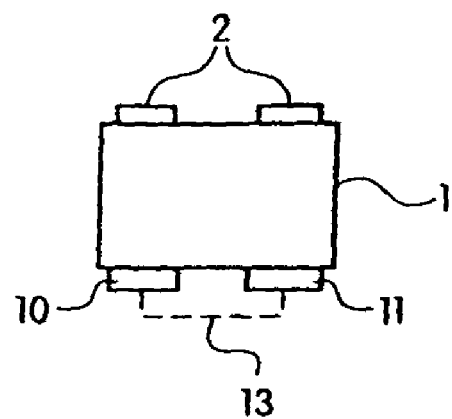
FIG. 5 shows an alternative embodiment of the device shown in FIG. 1.
Figure 6:
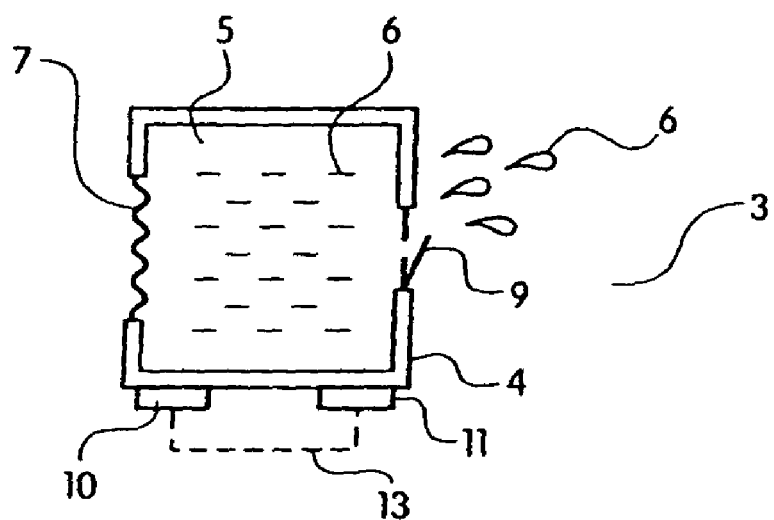
FIG. 6 shows an alternative embodiment of the device shown in FIG. 2.

In operation, the sensor 11 monitors physiological parameters of the tissue or organ being treated and senses changes in these physiological parameters. Upon sensing a change, the sensor 11 sends a signal to source 10 which, in response, generates an ultrasonic signal 8 for a period of time sufficient for the device to deliver the desired treatment to the tissue or organ being treated as previously discussed. The period of time that the ultrasonic signal 8 is generated may be fixed or may be selectively varied depending on the physiological change detected by the sensor 11 and may be varied as a function of the type and degree of physiological change detected by the sensor 11. In an especially preferred embodiment, the source 10 for ultrasonic vibration 8 may include a mechanism 12 for computing the amount of electricity or medicament required by the tissue or organ being treated as a function of the type and degree of physiological change detected by sensor 11. For example, by varying the duration of the ultrasonic vibration 8 generated, the device can control the amount of electricity or medicament delivered to the tissue or organ being treated. Thus, this embodiment provides a self-monitoring and self-delivering system that rapidly calculates the amount of treatment required and provides rapid delivery of the required amount treatment to the target area. The source 10 may also be disposed on the devices 1 and 3 as shown in FIGS. 5 and 6 to provide a self-contained monitoring, dosage-calculating, and dosage-administering system.

Alternatively, sensing may occur in one tissue, e.g., the brain or a nerve and the stimulation may occur in a different tissue, e.g., a paralyzed muscle. The devices and methods of this invention may be modified and adapted for a wide range of treatments as specific circumstances dictate, such as in cases of paralysis. For example, if a person's leg were paralyzed, a stimulator could be provided which would communicate with the muscles of the leg. The stimulator would generate a stimulus to the muscles in response to a sensor that could be located on, or communicate with, e.g., the person's arm. The sensor could be adapted to be responsive to movements of the individual's arm. Thus, when the individual wanted to activate the muscles of his leg he could do so by voluntarily moving his arm a predetermined distance or in a predetermined direction. The sensor in the arm would detect the degree of movement of the arm and transmit an activation signal for the stimulator, which, in turn, would apply the desire stimulation to the muscles in the person's leg. This permits the person to selectively generate a stimulus to the muscles and allow the person to selectively activate the muscles of his leg.

Figure 7:
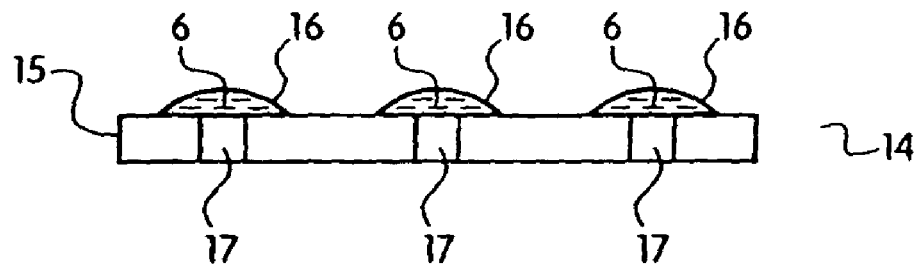
FIG. 7 shows an alternative embodiment of a device constructed in accordance with the invention for delivering a medicament to a target tissue.

FIG. 7 shows medicament delivery device 3 constructed in accordance with the invention for delivering a medicament to a target tissue. FIG. 7 shows that medicament delivery device 14 is provided with housing 15 provided with one or more medicament storage compartment bubbles 16 for storing a medicament 6. The bubbles 16 are constructed of a material well known to those skilled in the art that is selected and adapted to rupture in response to ultrasonic stimulation 8. The housing 15 may also be provided with one or more medicament ports 17 in fluid communication with the medicament storage compartment bubbles 16. The medicament ports 17 are adapted to permit a medicament 6 to be introduced into the medicament storage compartment bubbles 16. A wide variety of ports or valves well known to those skilled in the art as suitable for this purpose may be utilized as previously discussed.

In operation, the physician will introduce the medicament 6 into the medicament storage compartment bubbles 16 through the medicament port 11. The medicament delivery device 14 is then introduced into the target area using conventional procedures as previously discussed. The physician may selectively subject the medicament delivery device 14 to ultrasonic energy as previously discussed. The ultrasonic energy impinging upon the bubbles 16 causes the bubbles 16 to rupture. This causes the desired amount of medicament 6 to be discharged from the medicament storage compartment bubbles 16 to the target area. The amount of time that the device 14 is exposed to the ultrasonic vibration can be varied as specific applications dictate and will depend upon factors such as the target area to be treated, the quantity of medicament 6 to be delivered, the composition, e.g., solid or liquid and/or the viscosity of the medicament 6, and the type of material used to make the storage compartment bubbles 16. In an alternative embodiment, the medicament port is not utilized. Instead, the medicament 6 is disposed between the housing 15 and the bubbles 16 before the bubbles 16 are attached to the housing 15.

Figure 8:
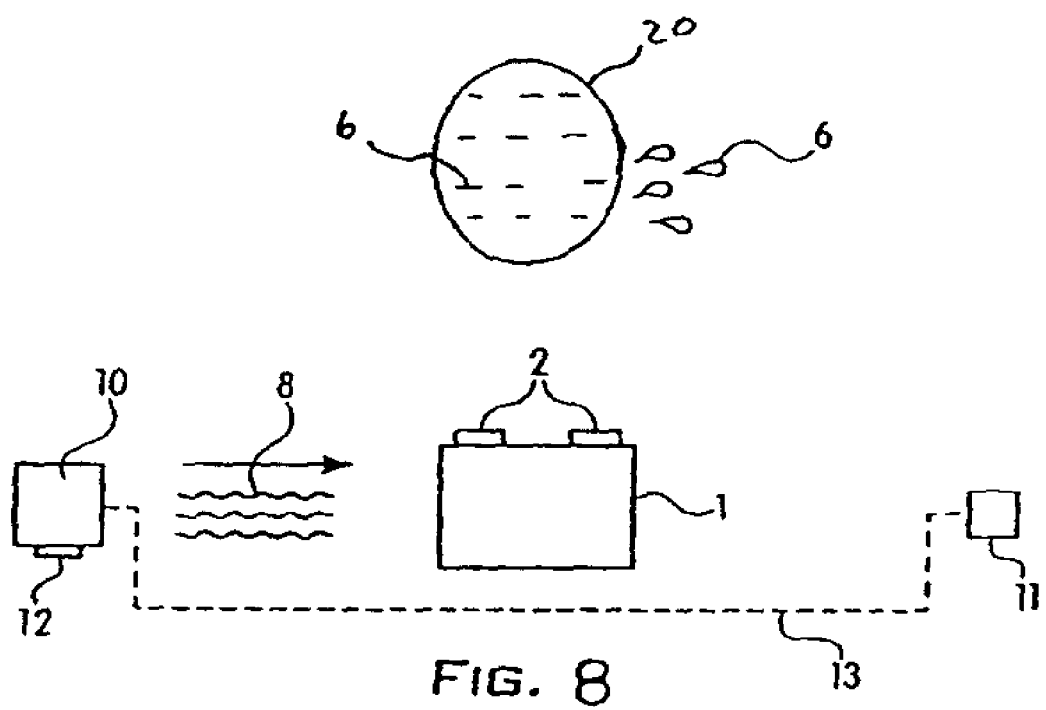
FIG. 8 shows another device constructed in accordance with the invention for applying electrical stimulation to a polymer containing the medicament for delivering the medicament to a target tissue or organ.

FIG. 8 shows another embodiment of a motor used in accordance with the invention to provide electrical stimulation to a polymer. The polymer in this embodiment again contains a medicament for release to a target tissue or organ. The polymer is preferably a biocompatible polymer such as, but not limited to, Poly Glycolic Acid (PGA) or Poly Lactic Acid (PLA). PGA and PLA are biocompatible, biodegradable, semi-crystalline polymers, which are approved for use in the human body. Polylactides and polyglycolides are currently used as absorbable suture material. The greatest advantage of using these polymers is that they degrade and break down into biologically acceptable molecules that are metabolized and removed from the body via normal metabolic pathways. Polylactides, polyglycolides, and their copolymers will eventually break down to lactic acid and glycolic acid, enter the Kreb's cycle, and be further broken down into carbon dioxide and water and excreted through normal bodily processes.

The basic structure, function and operation of elements 1, 2, 8, 10, 11, 12, and 13 of the embodiment in FIG. 8 are the same as the corresponding elements of FIG. 1. The medicament 6 to be released from a polymer microstructure 20 can be adsorbed within a volume of the polymer matrix or contained on the surface of the polymer. The strength of the binding of the medicament to the polymer is dependent on the charge of the polymer. Hence, by applying a current to the polymer and changing the polymer's electric charge, one can achieve a controlled release of the medicament from the polymer.

The desired medication can also be delivered to a localized tissue area by applying electrical current to the medicament, which in this embodiment is preferably a solution. When the electrical current is applied to the medicament, molecules having like electrical charges will repel each other. Therefore, application of a positive current will drive positively charged drug molecules away from the electrode and into the tissues; similarly, a negative current will drive negatively charge ions into the tissues. Unlike iontophoresis where the medicament is delivered through the skin, this invention provides for medicament delivery directly to the target tissues or organ.

Adverting to FIG. 8, once the electrical stimulation device 1 is in place, device 1 is subjected to ultrasonic vibrations or energy 8 from a source 10, which thereby cause the electrical stimulation device 1 to vibrate and generate electricity from the electrodes 2. The electrodes 2 may be sized and disposed on the device as specific applications dictate to maximize the effectiveness of the treatment. The electrical stimulation device 1 and the treatment time may be modified to generate electricity at a desired voltage and amperage and for a desired period of time as specific applications dictate. When the electric current is applied to the polymer, it causes the desired amount of medicament 6 to be discharged from the polymer microstructure 20 to the target area. The amount of time that the device 3 is exposed to the ultrasonic vibration 8 can be varied as specific applications dictate and will depend upon factors such as the target area to be treated, the quantity of medicament 6 to be delivered, and the particular characteristics of the medicament/polymer combination.

Figure 9:
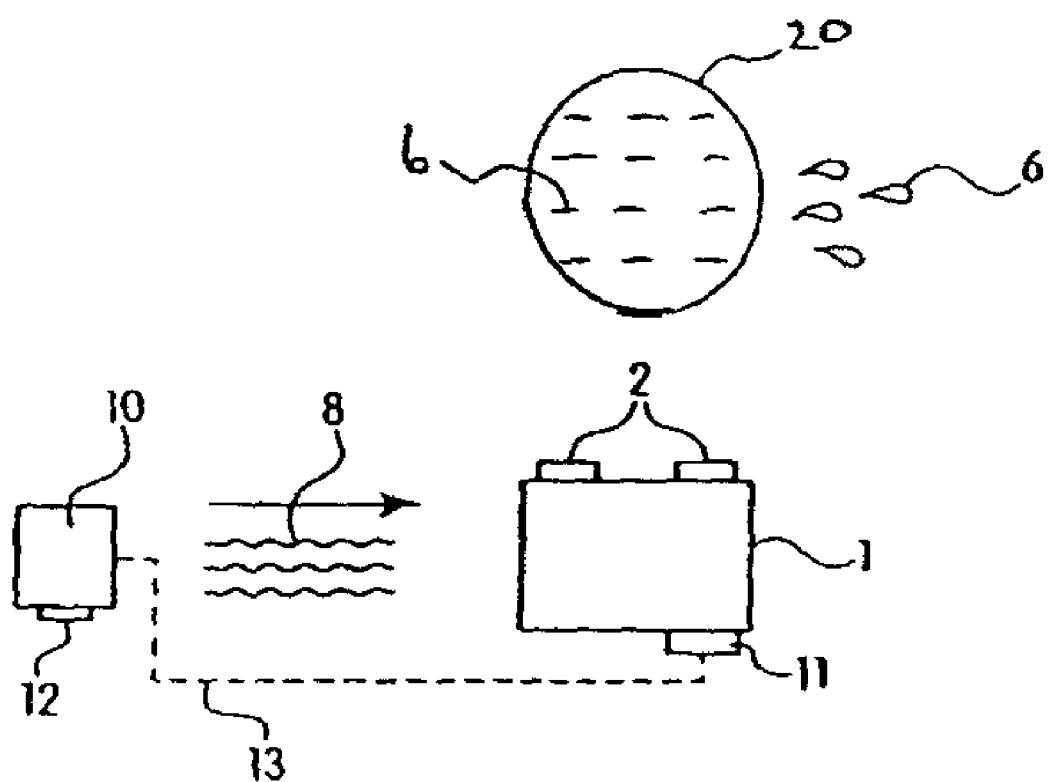
FIG. 9 shows another device constructed in accordance with the invention for delivering a medicament to a target tissue.
Figure 10:
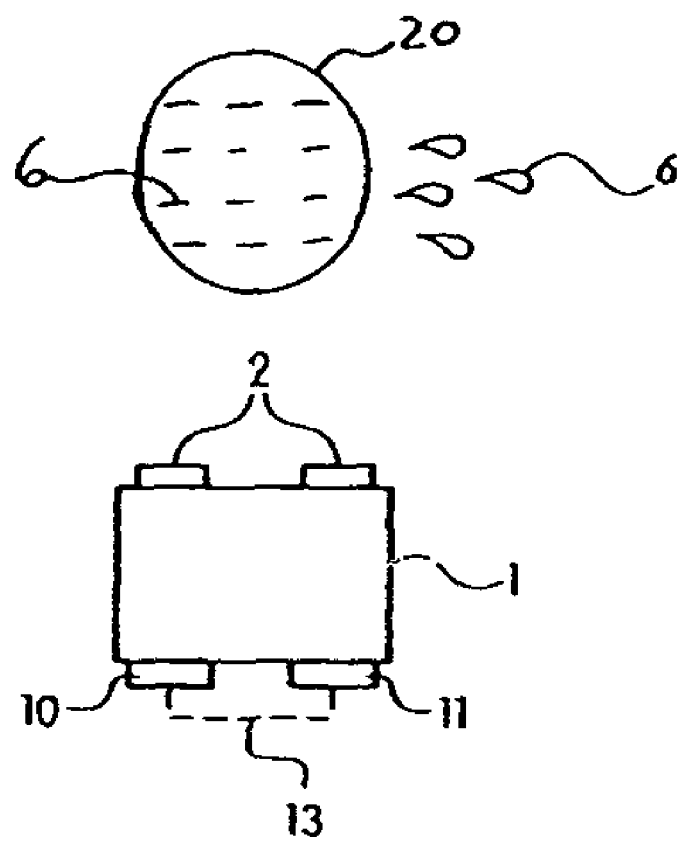
FIG. 10 shows an alternative embodiment of a device constructed in accordance with the invention for delivering a medicament to a target tissue.

As shown in FIGS. 8 to 10, and similar to the descriptions with references to FIGS. 1-7, one or more sensors 11 can be utilized in conjunction with the device 1 to monitor the tissue being treated for a variety of pre-selected physiological activities and parameters which indicate the need for treatment and the amount of treatment required. As shown in FIG. 9, the sensor 11 may be attached to the device 1. In addition, if desired, one or more sensors 11 can be implanted in any tissue or organ as appropriate. Depending on the embodiment, the sensor or sensors 11 may be implanted at several points about the tissue or organ being treated as specific applications dictate.

Figure 11:
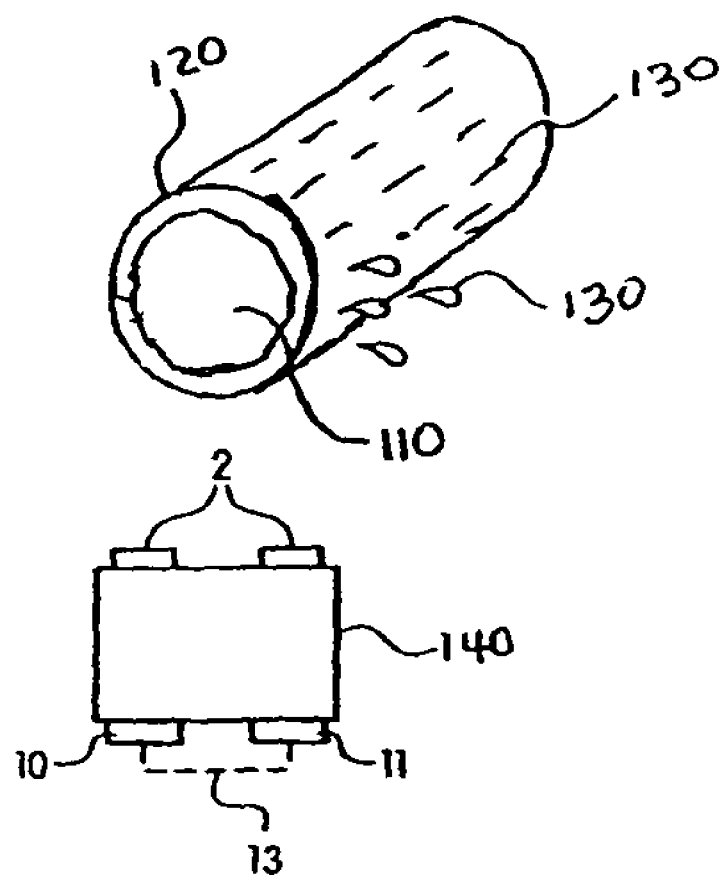
FIG. 11 shows an implant with a drug embedded polymer, and a source of current to charge the polymer in order to elute the drug.

FIG. 11 shows an implant 110 in the general shape of a rod. The implant can be any desired shape and is only depicted as a rod for illustrative purposes. The implant comprises of a polymer 120 embedded with a drug 130. A source 140 supplies current to charge the polymer to elute the drug from it. In this embodiment, the drug that has some electrical charge, and hence will be released from the polymer by the application a charge of similar polarity. The application of the same polar charge repels the drug out of the polymer and into the selected tissue.

The devices and procedures of this invention provide minimally invasive electrical and medicament stimulation of tissue with reduced risk of complications, e.g., infection that may result from conventional procedures. While the invention has been described with respect to a limited number of embodiments, it will be appreciated that many variations, modifications, and other applications of the invention may be made.

What is claimed is:

1. A method of treating bodily tissue or an organ, comprising:
    disposing an electrical stimulation device in the vicinity of the bodily tissue or organ to be treated; and
    subjecting the device to ultrasonic vibrations in an amount and for a period of time sufficient for the device to generate and transmit electrical currents at a preselected voltage and amperage, in the absence of a battery, to a polymer microstructure containing a medicament causing controlled release of the medicament from the polymer microstructure.

2. The method of claim 1, wherein the transmission of ultrasonic vibrations to the device is initiated in response to preselected stimuli generated by the bodily tissue.

3. The method of claim 2, further includes receiving the preselected stimuli generated by the body tissue through a sensor adapted to communicate with and selectively energize a means for selectively generating and transmitting the ultrasonic vibrations.

4. A method of treating bodily tissue or an organ, comprising:
    disposing an electrical stimulation device in the vicinity of the bodily tissue or organ to be treated,
    generating an electrical current from said device, having a preselected voltage and amperage, in response to ultrasonic vibrations;
    releasing a medicament from an implanted polymer material in response to said electrical current; and
    subjecting the device to ultrasonic vibrations in an amount and for a period of time sufficient for the device to generate and transmit electrical current at the preselected voltage and amperage, in the absence of a battery, required to release a preselected dosage of the medicament from the polymer.

5. The method of claim 4, wherein said electrical current is generated in response to preselected stimuli received from a different tissue than the bodily tissue to be treated.

6. The method of claim 4, wherein said electrical current is generated in response to preselected stimuli received from the bodily tissue to be treated.

7. The method of claim 4, wherein generating a positive electrical current drives positively charged medicament molecules away from the electrode and into the tissues.

8. The method of claim 4, wherein the releasing includes releasing the medicament from a cellular polymer microstructure in which the medicament is dispersed.

9. The method of claim 4, wherein releasing the medicament is from a polymer surface upon which the medicament is adsorbed.

10. A method of treating bodily tissue or an organ, comprising:
generating current from an implanted electrical stimulation device via piezoelectric effect, and applying said current to an implanted polymer embedded with a drug, the drug being electrically charged at a given polarity similar to the polarity of the applied current; and
eluting the drug from the polymer and into the bodily tissue being treated.

11. The method of claim 10, further includes disposing the device in the vicinity of a tissue or organ to be treated.

12. The method of claim 10, further includes receiving a preselected stimuli generated by a body tissue or organ through a sensor adapted to communicate with and selectively energize the device.

13. A method of treating body tissue, comprising the steps of:
receiving a signal from a sensor, said signal being a preselected stimuli generated by the body tissue;
selectively energizing a signal generator with said signal;
generating and transmitting ultrasonic vibrations from said signal generator to an electrical stimulation device;
generating and transmitting electrical current from said electrical stimulation device at a preselected voltage and amperage, in the absence of a battery, in response to said ultrasonic vibrations to an implanted polymer microstructure; and
releasing medicament from said implanted polymer microstructure, in a controlled release, said polymer implanted in the vicinity of the body tissue to be treated, thereby treating the body tissue.

14. The method of claim 13 wherein the electrical stimulation device is implanted in the vicinity of the body tissue to be treated.

15. The method of claim 13 wherein the sensor is implanted in the vicinity of the body tissue to be treated.

16. A method of treating body tissue comprising the steps of:
generating and transmitting ultrasonic vibrations from a signal generator to an electrical stimulation device thereby stimulating generation and transmission of an electrical current at a preselected voltage and amperage, in the absence of a battery, causing controlled release of a medicament from an implanted polymer containing said medicament, said polymer implanted in the vicinity of said body tissue to be treated, thereby treating said body tissue.

17. The method of claim 16 wherein said electrical stimulation device is implanted in the vicinity of the body tissue to be treated.

* * * * *